(12) United States Patent
Hudlicky et al.

US008981098B2

(10) Patent No.: US 8,981,098 B2
(45) Date of Patent: Mar. 17, 2015

(54) PROCESS FOR THE PREPARATION OF MORPHINE ANALOGS VIA THE REACTION OF ORGANOMETALLIC REAGENTS WITH AN OXAZOLIDINE DERIVED FROM MORPHINANS

(71) Applicants: Tomas Hudlicky, St. Catharines (CA); Mary Ann Endoma-Arias, St. Catharines (CA)

(72) Inventors: Tomas Hudlicky, St. Catharines (CA); Mary Ann Endoma-Arias, St. Catharines (CA)

(73) Assignee: Brock University, St. Catharines (CA)

( * ) Notice: Subject to any disclaimer, the term of this patent is extended or adjusted under 35 U.S.C. 154(b) by 0 days.

(21) Appl. No.: 14/374,397

(22) PCT Filed: Jan. 30, 2013

(86) PCT No.: PCT/CA2013/050072
§ 371 (c)(1),
(2) Date: Jul. 24, 2014

(87) PCT Pub. No.: WO2013/113120
PCT Pub. Date: Aug. 8, 2013

(65) Prior Publication Data
US 2014/0371458 A1    Dec. 18, 2014

Related U.S. Application Data

(60) Provisional application No. 61/594,678, filed on Feb. 3, 2012.

(51) Int. Cl.
| C07D 489/08 | (2006.01) |
| C07D 489/02 | (2006.01) |
| C07D 498/08 | (2006.01) |
| C07D 498/20 | (2006.01) |

(52) U.S. Cl.
CPC ............ *C07D 498/08* (2013.01); *C07D 489/08* (2013.01); *C07D 498/20* (2013.01)
USPC .................................. 546/44; 546/39; 546/45

(58) Field of Classification Search
USPC .................................................. 546/44, 39, 45
See application file for complete search history.

(56) References Cited

U.S. PATENT DOCUMENTS

| 2005/0182258 A1 | 8/2005 | Schimidhammer |
| 2012/0283443 A1 * | 11/2012 | Hudlicky et al. ............... 546/39 |

FOREIGN PATENT DOCUMENTS

| WO | 2005028483 A1 | 3/2005 |
| WO | 2009067275 A1 | 5/2009 |
| WO | 2010121369 A1 | 10/2010 |
| WO | 2012149633 A1 | 11/2012 |

OTHER PUBLICATIONS

International Preliminary Search Report and Written Opinion of PCT/CA2013/050072 dated Aug. 5, 2014.

* cited by examiner

*Primary Examiner* — Charanjit Aulakh
(74) *Attorney, Agent, or Firm* — Bereskin & Parr LLP/S.E.N.C.R.L., s.r.l.; Patricia Folkins

(57) ABSTRACT

The oxazolidine derived from the reaction of oxymorphone with the Burgess reagent, temporarily protected at O-3 and C-6, reacts with Grignard or other suitable metallic or organometallic reagents to directly provide, for example, A/-allyl, A/-methylcyclopropyl and /V-methylcyclobutyl derivatives that are further converted into naltrexone, naloxone, nalbuphone and nalbuphine in excellent yields. These morphine analogs can be prepared from the oxazolidine in a one-pot synthesis.

24 Claims, No Drawings

PROCESS FOR THE PREPARATION OF MORPHINE ANALOGS VIA THE REACTION OF ORGANOMETALLIC REAGENTS WITH AN OXAZOLIDINE DERIVED FROM MORPHINANS

CROSS-REFERENCE TO RELATED APPLICATIONS

The present application is a National Stage of co-pending International Application No. PCT/CA2013/050072 filed on Jan. 30, 2013, which claims the benefit of priority from U.S. provisional application No. 61/594,678 filed on Feb. 3, 2012, the contents of both of which are incorporated herein by reference in their entirety.

FIELD OF THE APPLICATION

The present application relates to new processes useful in the preparation of morphine analogs such as naloxone, naltrexone, nalbuphone and nalbuphine via the reaction of a Grignard, or other suitable organometallic or metallic reagent, with an oxazolidine derived from a morphinan.

BACKGROUND OF THE APPLICATION

Various opiate-derived antagonists such as naloxone, naltrexone, nalbuphone and nalbuphine are prepared by semi-synthesis from natural opiates such as morphine, thebaine or oripavine, Scheme 1. These compounds are used extensively in medicine as antagonists (naltrexone and naloxone) or mixed agonist/antagonist (nalbuphine). Naltrexone is used in the treatment of alcoholism and opioid dependence. Naloxone is the active ingredient in Narcan® for the reversal of opioid overdose and is also used in combination with buprenorphine (Suboxone®) for the treatment of opioid addiction. It is also employed with tilidine (Valoron N®) for the treatment of pain and with oxycodone (Targin®) for the prophylaxis and/or treatment of opioid-induced constipation. Nalbuphine is the active ingredient in Nubain®, which is used as an analgesic.

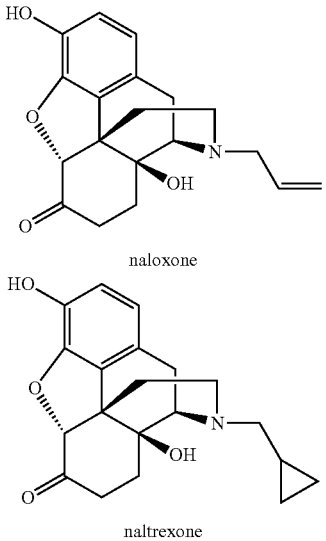

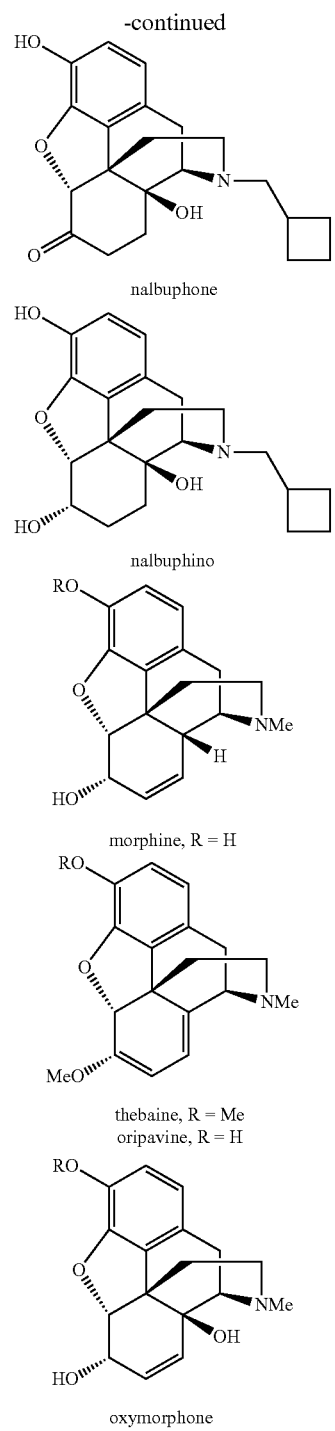

The synthesis of compounds such as naloxone, naltrexone and nalbuphone requires the oxidation of natural opiate alkaloids at the C-14 position. The synthesis of compounds such as naloxone, naltrexone, nalbuphone and nalbuphine requires the eventual replacement of an N-methyl group with, for example, an allyl, methylcyclopropyl, methylcyclobutyl, or other group. The synthesis of naloxone, naltrexone, nalbuphone and nalbuphine by several methods differing in concept as well as execution has been reported.

For example, naltrexone as well as R-methylnaltrexone, were prepared by N-demethylation of quaternary salts derived from oripavine followed by oxidation of N-methylcyclopropyl nororipavine.[1] Similarly, nalbuphone and nalbuphine became available.[2] N-Methylcyclopropyl nororipavine served as a convenient starting material for the improved synthesis of buprenorphine.[3] Buprenorphine was also synthesized from oripavine by a newly discovered palladium-catalyzed N-demethylation/acylation protocol.[4] In addition, it has been reported that the N-oxide of oxymorphone is easily demethylated with the Burgess reagent and that the intermediate iminium ion is trapped to form oxazolidines a and b in excellent yield and in a one-pot sequence from oxymorphone, as shown in Scheme 2.[5]

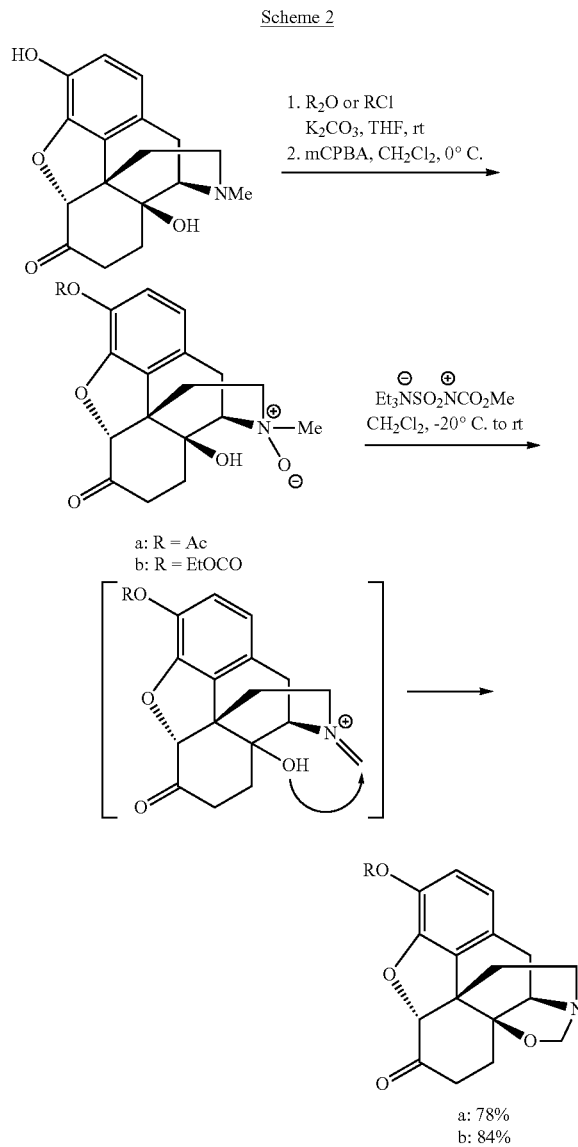

a: R = Ac
b: R = EtOCO a: 78%
b: 84%

All of these efforts were the result of a focused program implemented to discover more efficient and environmentally friendly methods for the replacement of the N-methyl group in natural opiates with the appropriate alkyl group required for the medicinal agents.

SUMMARY OF THE APPLICATION

A comparison of overall efficiency and the potential for scale-up by process groups of above-described processes has now been undertaken. The above-mentioned N-demethylation protocols for naltrexone and methylnaltrexone were found to be suitable for process scale-up. However, the N-demethylation of quaternary salts containing an N-allyl group could not be used for the synthesis of naloxone, as the treatment of such salts with nucleophiles would lead to N-deallylation rather than N-demethylation. Nucleophilic cleavage of oxazolidines containing, for example, a suitably protected C-6 ketone was therefore investigated.

If an oxazolidine derived from, for example, the reaction shown in Scheme 2, could be cleaved by a suitable organometallic reagent, for example a suitable Grignard, organolithium, organocuprate, organozinc or organoaluminum reagent, or other suitable metallic reagent, then the original N-methyl group carbon would remain in the product, and the process for the synthesis of naloxone and other derivatives would be more atom economical. The present application reports a general method of synthesis for naloxone, naltrexone, nalbuphone, nalbuphine and other morphine analogs via oxazolidines derived from, for example, oxymorphone.

Accordingly, the present application includes a process for the preparation of a compound of Formula I:

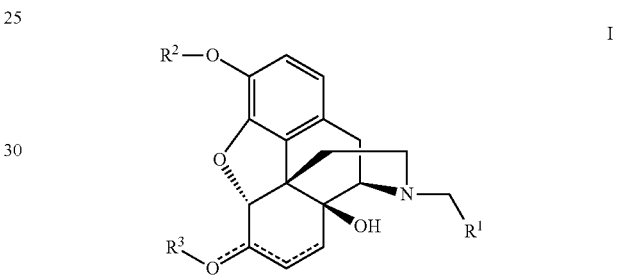

wherein
⸺ represents a single or double bond, provided that two double bonds are not adjacent to each other;
$R^1$ is selected from $C_{3-10}$cycloalkyl, $C_{3-10}$cycloalkenyl, $C_{1-10}$alkyl, $C_{2-10}$alkenyl, $C_{6-10}$aryl, $C_{1-10}$alkyleneC$_{6-10}$aryl and $C_{1-10}$alkyleneC$_{3-10}$cycloalkyl; and
$R^2$ and $R^3$ are independently selected from H, $C_{1-10}$alkyl, $C_{1-10}$acyl, $C_{6-10}$aryl, $C_{3-10}$cycloalkyl, $C_{1-10}$alkyleneC$_{6-10}$aryl and $C_{1-10}$alkyleneC$_{3-10}$cycloalkyl, except when ⸺ O represents ═O, then $R^3$ is not present;
comprising
(a) reacting a compound of Formula II or a protected form thereof:

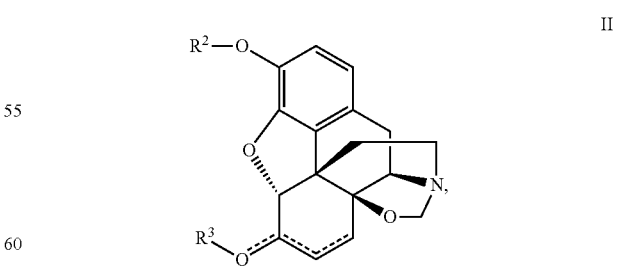

wherein
⸺ represents a single or double bond, provided that two double bonds are not adjacent to each other; and
$R^2$ and $R^3$ are independently selected from H, $C_{1-10}$alkyl, $C_{1-10}$acyl, $C_{6-10}$aryl, $C_{3-10}$cycloalkyl, $C_{1-10}$alkyleneC$_{6-10}$aryl and $C_{1-10}$alkylene$C_{3-10}$cycloalkyl, except when ⚌O represents =O, then $R^3$ is not present;
with a reagent of Formula III:

$$R^1A \qquad \qquad III,$$

wherein $R^1$ is selected from $C_{1-10}$alkyl, $C_{2-10}$alkenyl, $C_{3-10}$cycloalkyl, $C_{3-10}$cycloalkenyl, $C_{6-10}$aryl, $C_{1-10}$alkylene$C_{6-10}$aryl and $C_{1-10}$alkylene$C_{3-10}$cycloalkyl; and
A is a suitable metallic or organometallic countercation; and
(b) optionally deprotecting the compound derived from reacting the compound of Formula II or protected form thereof with the reagent of Formula III;
under conditions to provide a compound of Formula I;
wherein in the compounds of Formulae I, II and III one or more available hydrogens in $R^1$, $R^2$ and $R^3$ is/are optionally replaced with F and/or one or more of available atoms in $R^1$, $R^2$ and $R^3$ is/are optionally replaced with an isotopic label.

Other features and advantages of the present application will become apparent from the following detailed description. It should be understood, however, that the detailed description and the specific examples while indicating embodiments of the application are given by way of illustration only, since various changes and modifications within the spirit and scope of the application will become apparent to those skilled in the art from this

DETAILED DESCRIPTION DETAILED DESCRIPTION OF THE APPLICATION

I. Definitions

Unless otherwise indicated, the definitions and embodiments described in this and other sections are intended to be applicable to all embodiments and aspects of the application herein described for which they are suitable as would be understood by a person skilled in the art.

As used in this application, the singular forms "a", "an" and "the" include plural references unless the content clearly dictates otherwise. For example, an embodiment including "a reducing agent" should be understood to present certain aspects with one reducing agent, or two or more additional reducing agents.

In embodiments comprising an "additional" or "second" component, such as an additional or second reducing agent, the second component as used herein is chemically different from the other components or first component. A "third" component is different from the other, first, and second components, and further enumerated or "additional" components are similarly different.

The term "suitable" as used herein means that the selection of the particular compound or conditions would depend on the specific synthetic manipulation to be performed, and the identity of the molecule(s) to be transformed, but the selection would be well within the skill of a person trained in the art. All process/method steps described herein are to be conducted under conditions sufficient to provide the product shown. A person skilled in the art would understand that all reaction conditions, including, for example, reaction solvent, reaction time, reaction temperature, reaction pressure, reactant ratio and whether or not the reaction should be performed under an anhydrous or inert atmosphere, can be varied to optimize the yield of the desired product and it is within their skill to do so.

In embodiments of the application, the compounds described herein have at least one asymmetric centre. Where compounds possess more than one asymmetric centre, they may exist as diastereomers. It is to be understood that all such isomers and mixtures thereof in any proportion are encompassed within the scope of the present application. It is to be further understood that while the stereochemistry of the compounds may be as shown in any given compound listed herein, such compounds may also contain certain amounts (e.g. less than 20%, suitably less than 10%, more suitably less than 5%) of compounds of the application having alternate stereochemistry.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers and/or steps. The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps.

Terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

The term "Burgess reagent" as used herein refers to a reagent of the formula:

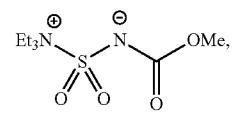

also known as methyl N-(triethylammoniumsulfonyl)carbamate. This reagent is commercially available (for example from Sigma Aldrich, St. Louis, Mo., USA) or may be prepared from chlorosulfonylisocyanate by treatment with methanol, followed by triethylamine in benzene.[6]

The term "countercation" as used herein refers to a positively charged species consisting of a single element, or a positively charged species consisting of a group of elements connected by ionic and/or covalent bonds.

The term "Grignard reagent" as used herein refers to a reagent of Formula III, wherein A is MgX; i.e. a reagent of the formula $R^1MgX$, wherein X is selected from Cl, Br and I, and $R^1$ is as defined herein. Such reagents may be commercially available (for example from Sigma-Aldrich Co.) and/or they may be prepared from the reaction of a suitable organohalide with a suitable source of magnesium metal under conditions suitable for the formation of the required Grignard reagent. The selection of a suitable synthetic route to the Grignard reagent required can be made by a person skilled in the art. A number of synthetic routes are known in the art, for example as described in Smith, M. B. and March, J., "March's Advanced Organic Chemistry Reactions, Mechanisms and Structure" 5th ed., John Wiley & Sons, Inc., 2001 (New York) at, for example, pages 805ff.

The term "organolithium reagent" as used herein refers to a reagent of Formula III, wherein A is Li; i.e. a regent of the formula $LiR^1$, wherein $R^1$ is as defined herein. Such reagents may be commercially available (for example from Sigma-Aldrich Co.) and/or they may be prepared, for example, from the reaction of a suitable organohalide with lithium metal or by halogen-metal exchange using suitable reagents under conditions suitable for the formation of the required organolithium reagent. The selection of a suitable synthetic route to the organolithium reagent required can be made by a person skilled in the art. A number of synthetic routes are known in the art, for example as described in Loudon, G. M., "Organic Chemistry" Addison-Wesley Publishing Company, 1984 (Reading, Mass.) at, for example, page 652.

The term "organocuprate reagent" as used herein refers to a reagent of Formula III, wherein A is $LiCuL^1$; i.e. a reagent of the formula $R^1L^1CuLi$, wherein $R^1$ is as defined herein and $L^1$ is selected from $C_{1-10}$alkyl, $C_{2-10}$alkenyl, $C_{3-10}$cycloalkyl, $C_{3-10}$cycloalkenyl, $C_{6-10}$aryl, $C_{1-10}$alkylene$C_{6-10}$aryl and $C_{1-10}$alkylene$C_{3-10}$cycloalkyl. Such reagents may be prepared from, for example, the reaction of about two equivalents of a suitable organolithium reagent with about one equivalent of CuCl under conditions suitable for the formation of the required organocuprate reagent. The selection of a suitable synthetic route to the organocuprate reagent required can be made by a person skilled in the art. Synthetic routes are known in the art, for example as described in Loudon, G. M., "Organic Chemistry" Addison-Wesley Publishing Company, 1984 (Reading, Mass.) at, for example, page 345.

The term "organozinc" reagent as used herein refers to a reagent of Formula III, wherein A is $ZnL^2$; i.e. a reagent of the formula $ZnR^1L^2$, wherein $R^1$ is as defined herein, and each $L^2$ is independently selected from Cl, Br, I, $C_{1-10}$alkyl, $C_{2-10}$alkenyl, $C_{3-10}$cycloalkyl, $C_{3-10}$cycloalkenyl, $C_{6-10}$aryl, $C_{1-10}$alkylene$C_{6-10}$aryl and $C_{1-10}$alkylene$C_{3-10}$cycloalkyl. Such reagents may be commercially available (for example from Sigma-Aldrich Co.) and/or they may be prepared, for example, from the reaction of a suitable organohalide with a suitable source of zinc metal under conditions suitable for the formation of the required organozinc reagent. The selection of a suitable synthetic route to the organozinc reagent required can be made by a person skilled in the art. A number of synthetic routes are known in the art, for example as described in Smith, M. B. and March, J., "March's Advanced Organic Chemistry: Reactions, Mechanisms and Structure" 5th ed., John Wiley & Sons, Inc., 2001 (New York) at, for example, pages 805ff.

The term "organoaluminum reagent" as used herein refers to a reagent of Formula III, wherein A is $Al(L^3)_2$; i.e. a reagent of the formula $AlR^1(L^3)_2$, wherein $R^1$ is as defined herein, and each $L^3$ is independently selected from Cl, Br, I, $C_{1-10}$alkyl, $C_{2-10}$alkenyl, $C_{3-10}$cycloalkyl, $C_{3-10}$cycloalkenyl, $C_{6-10}$aryl, $C_{1-10}$alkylene$C_{6-10}$aryl and $C_{1-10}$alkylene$C_{3-10}$cycloalkyl. Such reagents may be commercially available (for example from Sigma-Aldrich Co.) and/or they may be prepared from the reaction of suitable reagents. A number of synthetic routes are known in the art, for example, as described in Downs, A. J., "Chemistry of Aluminium, Gallium, Indium and Thallium" Chapman & Hall, 1993 (London, UK) at, for example, page 324ff. The selection of a suitable synthetic route to the organoaluminum regent required can be made by a person skilled in the art.

The term "ketone activating reagent" as used herein refers to a reagent that catalyzes the reaction between a suitable ketone and a suitable alcohol to form the corresponding ketal. The selection of a suitable ketone activating reagent can be made by a person skilled in the art. A number of ketone activating reagents are known in the art, for example as described in Smith, M. B. and March, J., "March's Advanced Organic Chemistry: Reactions, Mechanisms and Structure" 5th ed., John Wiley & Sons, Inc., 2001 (New York) at, for example, pages 1180ff. It is an embodiment of the application that the ketone activating reagent is a silyl chloride, such as trimethylsilyl chloride (TMSCl).

The term "acyl" as used herein, whether it is used alone or as part of another group, means straight or branched chain, saturated acyl groups. The term $C_{1-6}$acyl means an acyl group having 1, 2, 3, 4, 5 or 6 carbon atoms. It is an embodiment of the application that, in the acyl groups, one or more, including ail of the available hydrogen atoms are optionally replaced with F or $^2H$ and thus include, for example trifluoroacetyl and the like.

The term "alkyl" as used herein, whether it is used alone or as part of another group, means straight or branched chain, saturated alkyl groups. The term $C_{1-6}$alkyl means an alkyl group having 1, 2, 3, 4, 5, or 6 carbon atoms. It is an embodiment of the application that, in the alkyl groups, one or more, including all, of the hydrogen atoms are optionally replaced with F or $^2H$ and thus include, for example trifluoromethyl, pentafluoroethyl and the like.

The term "alkylene" as used herein, whether it is used alone or as part of another group, refers to a bivalent alkyl group.

The term "alkenyl" as used herein, whether it is used alone or as part of another group, means straight or branched chain, unsaturated alkenyl groups. The term $C_{2-6}$alkenyl means an alkenyl group having 2, 3, 4, 5, or 6 carbon atoms and at least one double bond. It is an embodiment of the application that, in the alkenyl groups, one or more, including all, of the hydrogen atoms are optionally replaced with F or $^2H$ and thus include, for example trifluoroethenyl, pentafluoropropenyl and the like.

The term "cycloalkyl" as used herein, whether it is used alone or as part of another group, means cyclic, saturated alkyl groups. The term $C_{3-10}$cycloalkyl means a cycloalkyl group having 3, 4, 5, 6, 7, 8, 9 or 10 carbon atoms. It is an embodiment of the application that, in the cycloalkyl groups, one or more, including all, of the hydrogen atoms are optionally replaced with F or $^2H$.

The term "cycloalkenyl" as used herein, whether it is used alone or as part of another group, means cyclic, unsaturated alkyl groups. The term $C_{3-10}$cycloalkenyl means a cycloalkenyl group having 3, 4, 5, 6, 7, 8, 9 or 10 carbon atoms and at least one double bond. It is an embodiment of the application that, in the cycloalkenyl groups, one or more, including all, of the hydrogen atoms are optionally replaced with F or $^2H$.

The term "aryl" as used herein refers to cyclic groups that contain at least one aromatic ring. In an embodiment of the application, the aryl group contains from 6, 9 or 10 atoms, such as phenyl, naphthyl or indanyl. It is an embodiment of the application that, in the aryl groups, one or more, including all, of the hydrogen atoms are optionally replaced with F or $^2H$ and thus include, for example pentafluorophenyl and the like.

The term "halo" as used herein refers to a halogen atom and includes F, Cl, Br and I.

The term "reducing agent" as used herein means any compound or combination of compounds that reduces a desired functional group(s) but does not otherwise react with or degrade the substrate comprising the functional group(s). A reducing agent results in the overall gain of electrons, or in the case of organic chemistry, hydrogen atoms to the functional group.

tBoc as used herein refers to the group t-butyloxycarbonyl.

Ac as used herein refers to the group acetyl.

Ts (tosyl) as used herein refers to the group p-toluenesulfonyl.

Ms as used herein refers to the group methanesulfonyl.

TBDMS as used herein refers to the group t-butyldimethylsilyl.

TBDPS as used herein refers to the group t-butyldiphenylsilyl.

TMS as used herein refers to the group trimethylsilyl.

Tf as used herein refers to the group trifluoromethanesulfonyl.

Ns as used herein refers to the group naphthalene sulphonyl.

Bn as used herein refers to the group benzyl.

Fmoc as used herein refers to the group fluorenylmethoxycarbonyl.

mCPBA as used herein refers to meta-chloroperbenzoic acid.

THF as used herein refers to the compound tetrahydrofuran.

The terms "protective group" or "protecting group" or "PG" or the like as used herein refer to a chemical moiety which protects or masks a reactive portion of a molecule to prevent side reactions in those reactive portions of the molecule, while manipulating or reacting a different portion of the molecule. After the manipulation or reaction is complete, the protecting group is removed under conditions that do not degrade or decompose the remaining portions of the molecule. The selection of a suitable protecting group can be made by a person skilled in the art. Many conventional protecting groups are known in the art, for example as described in "Protective Groups in Organic Chemistry" McOmie, J. F. W. Ed., Plenum Press, 1973, in Greene, T. W. and Wuts, P. G. M., "Protective Groups in Organic Synthesis", John Wiley & Sons, 3$^{rd}$ Edition, 1999 and in Kocienski, P. Protecting Groups, 3rd Edition, 2003, Georg Thieme Verlag (The Americas). Examples of suitable protecting groups include, but are not limited to t-Boc, Ac, Ts, Ms, silyl ethers such as TMS, TBDMS, TBDPS, Tf, Ns, Bn, Fmoc, benzoyl, dimethoxytrityl, methoxyethoxymethyl ether, methoxymethyl ether, pivaloyl, p-methoxybenzyl ether, tetrahydropyranyl, trityl, ethoxyethyl ethers, carbobenzyloxy, benzoyl and the like.

The expression "proceed to a sufficient extent" as used herein with reference to the reactions or process steps disclosed herein means that the reactions or process steps proceed to an extent that conversion of the starting material or substrate to product is maximized. Conversion may be maximized when greater than about 5, 10, 15, 20, 25, 30, 35, 40, 45, 50, 55, 60, 65, 70, 75, 80, 85, 90, 95 or 100% of the starting material or substrate is converted to product.

II. Methods of the Application

The present application includes a process for the preparation of a compound of Formula I:

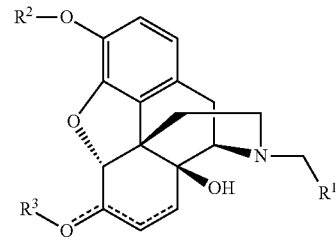

wherein

═══ represents a single or double bond, provided that two double bonds are not adjacent to each other;

$R^1$ is selected from $C_{3-10}$cycloalkyl, $C_{3-10}$cycloalkenyl, $C_{1-10}$alkyl, $C_{2-10}$alkenyl, $C_{6-10}$aryl, $C_{1-10}$alkyleneC$_{6-10}$aryl and $C_{1-10}$alkyleneC$_{3-10}$cycloalkyl; and $R^2$ and $R^3$ are independently selected from H, $C_{1-10}$alkyl, $C_{1-10}$acyl, $C_{6-10}$aryl, $C_{3-10}$cycloalkyl, $C_{1-10}$alkyleneC$_{6-10}$aryl and $C_{1-10}$alkyleneC$_{3-10}$cycloalkyl, except when ═══ O represents ═O, then $R^3$ is not present;

comprising (a) reacting a compound of Formula II or a protected form thereof:

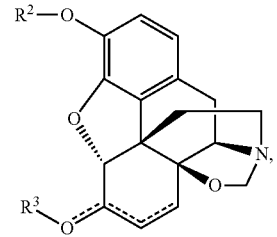

wherein

═══ represents a single or double bond, provided that two double bonds are not adjacent to each other; and $R^2$ and $R^3$ are independently selected from H, $C_{1-10}$alkyl, $C_{1-10}$acyl, $C_{6-10}$aryl, $C_{3-10}$cycloalkyl, $C_{1-10}$alkyleneC$_{6-10}$aryl and $C_{1-10}$alkyleneC$_{3-10}$cycloalkyl, except when ═══ O represents ═O, then $R^3$ is not present;

with a reagent of Formula III:

$R^1$A III, wherein $R^1$ is selected from $C_{1-10}$alkyl, $C_{2-10}$alkenyl, $C_{3-10}$cycloalkyl, $C_{3-10}$cycloalkenyl, $C_{6-10}$aryl, $C_{1-10}$alkyleneC$_{6-10}$aryl and $C_{1-10}$alkyleneC$_{3-10}$cycloalkyl; and A is a suitable metallic or organometallic countercation; and (b) optionally deprotecting the compound derived from reacting the compound of Formula II or protected form thereof with the reagent of Formula III;

under conditions to provide a compound of Formula I;

wherein in the compounds of Formulae I, II and III one or more available hydrogens in $R^1$, $R^2$ and $R^3$ is/are optionally replaced with F and/or one or more of available atoms in $R^1$, $R^2$ and $R^3$ is/are optionally replaced with an isotopic label.

In an embodiment of the application $R^1$ is selected from $C_{1-6}$alkyl, $C_{2-6}$alkenyl, $C_{3-6}$cycloalkyl, $C_{3-6}$cycloalkenyl, $C_{6-10}$aryl, $C_{1-6}$alkyleneC$_{6-10}$aryl, and $C_{1-6}$alkyleneC$_{3-6}$cycloalkyl. In another embodiment of the application, $R^1$ is selected from Me, Et, vinyl, allyl, Ph, cyclopropyl, cyclobutyl, cyclopentyl, cyclohexyl, Bn, cyclopropylmethyl, cyclobutylmethyl, cyclopentylmethyl and cyclohexylmethyl.

It is a further embodiment of the application that $R^1$ is selected from vinyl, cyclopropyl and cyclobutyl.

In an embodiment of the application $R^2$ and $R^3$ are independently selected from H, $C_{1-6}$alkyl, $C_{1-6}$acyl, $C_{6-10}$aryl, $C_{3-6}$cycloalkyl, $C_{3-6}$cycloalkenyl, $C_{1-6}$alkylene$C_{6-10}$aryl, and $C_{1-6}$alkylene$C_{3-6}$cycloalkyl. In a further embodiment of the application, $R^2$ and $R^3$ are independently selected from H, Ac, Me, Et, Ph, cyclobutyl, cyclopentyl, cyclohexyl, Bn, cyclobutylmethyl, cyclopentylmethyl and cyclohexylmethyl. It is an embodiment of the application that $R^2$ is Ac. In another embodiment of the application, $R^3$ is H.

In an embodiment of the application, the reagent of Formula III; i.e. the reagent of formula $R^1A$ is selected from a Grignard reagent, an organolithium reagent, an organocuprate reagent, an organozinc reagent and an organoaluminum reagent. It is an embodiment of the application that $R^1A$ is a Grignard reagent of formula $R^1MgX$, wherein X is selected from Cl, Br and I. In a further embodiment of the application, X is selected from Cl and Br. It is an embodiment that X is Br.

In an embodiment, the compound of Formula II is selected from a compound of Formula II(a), II(b) and II(c):

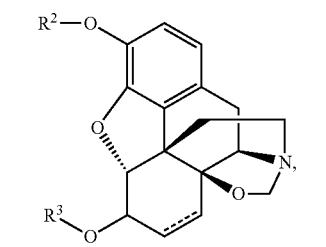

II(a)

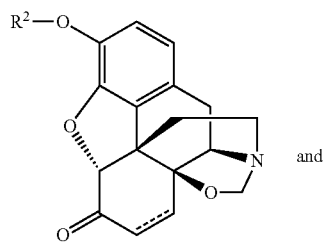

II(b)

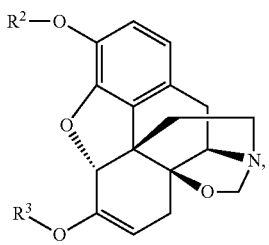

II(c)

wherein

▃▃▃ represents a single or double bond; and $R^2$ and $R^3$ are independently selected from H, $C_{1-10}$alkyl, $C_{1-10}$acyl, $C_{6-10}$aryl, $C_{3-10}$cycloalkyl, $C_{1-10}$alkylene$C_{6-10}$aryl, and $C_{1-10}$alkylene$C_{3-10}$cycloalkyl, which provide, respectively, a compound of Formula I(a), I(b) and I(c) using the process of the present application:

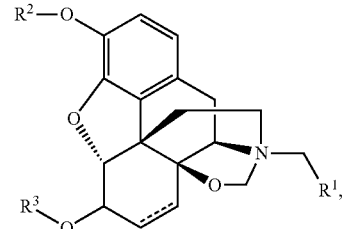

I(a)

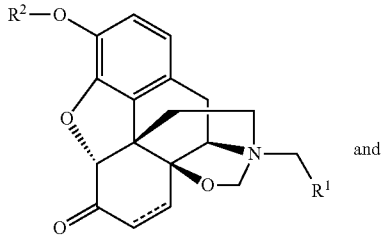

I(b)

and

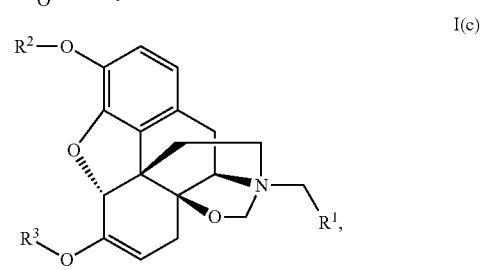

I(c)

wherein

▃▃▃ represents a single or double bond;

$R^1$ is selected from $C_{1-10}$alkyl, $C_{2-10}$alkenyl, $C_{3-10}$cycloalkyl, $C_{3-10}$cycloalkenyl, $C_{6-10}$aryl, $C_{1-10}$alkylene$C_{6-10}$aryl and $C_{1-10}$alkylene$C_{3-10}$cycloalkyl;

$R^2$ and $R^3$ are independently selected from H, $C_{1-10}$alkyl, $C_{1-10}$acyl, $C_{6-10}$aryl, $C_{3-10}$cycloalkyl, $C_{1-10}$alkylene $C_{6-10}$aryl, and $C_{1-10}$alkylene$C_{3-10}$cycloalkyl; and wherein in the compounds of Formulae I(a), I(b), I(c), II(a), II(b) and II(c) one or more available hydrogens in $R^1$, $R^2$ and $R^3$ is/are optionally replaced with F and/or one or more of available atoms in $R^1$, $R^2$ and $R^3$ is/are optionally replaced with an isotopic label.

In an embodiment of the application, the conditions to provide the compounds of Formula I from the compounds of Formula II using the reagents of Formula III comprise adding the reagent of Formula III dropwise to a stirred solution of the oxazolidine of Formula II in a suitable solvent, for example, THF, at about −5° C. to about 5° C., or about 0° C., allowing the mixture to warm up to a temperature of about 0° C. to about 30° C., or about room temperature, and stirring for a time for the conversion of the compound of Formula II to the compound of Formula I to proceed to a sufficient extent, for example, about 1.5 hours to about 6 hours, or about 2 hours, at which time the mixture is quenched with a suitable reagent, for example, saturated $NH_4Cl$ solution. In an embodiment, the molar ratio of the reagent of Formula III to the compound of Formula II is about 3:1 to about 8:1 or about 5:1.

In an embodiment, the compound of Formula III is selected from a compound of Formula III(i), III(ii) and III(iii):

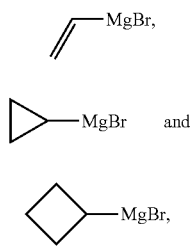
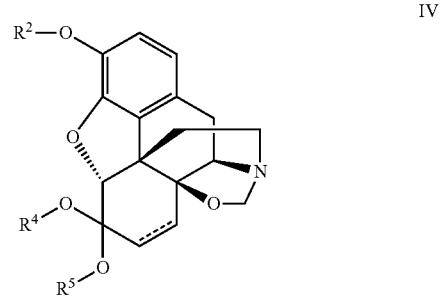

which provide, respectively, a compound of Formula I(i), I(ii) and I(iii) using the process of the present application:

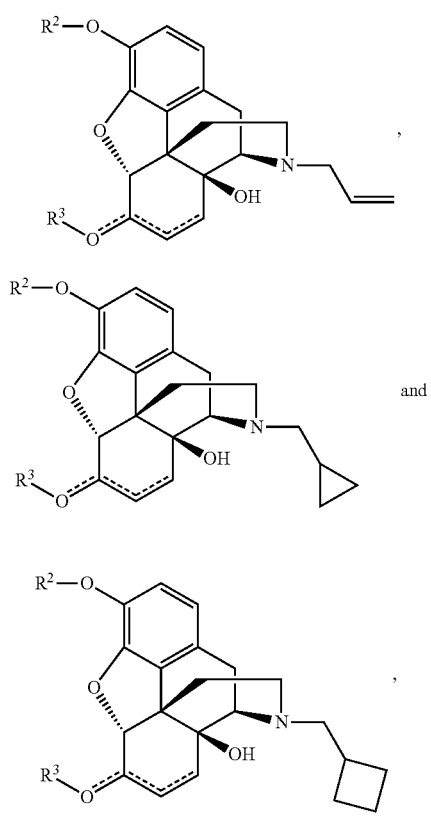

wherein

⁓ represents a single or double bond, provided that two double bonds are not adjacent to each other;

$R^2$ and $R^3$ are independently selected from H, $C_{1-10}$alkyl, $C_{1-10}$acyl, $C_{6-10}$aryl, $C_{3-10}$cycloalkyl, $C_{1-10}$alkylene$C_{6-10}$aryl and $C_{1-10}$alkylene$C_{3-10}$cycloalkyl, except when ⁓ O represents =O, then $R^3$ is not present; and wherein in the compounds of Formulae I(i), I(ii) and I(iii), one or more available hydrogens in $R^2$ and $R^3$ is/are optionally replaced with F and/or one or more of available atoms in $R^2$ and $R^3$ is/are optionally replaced with an isotopic label.

In an embodiment, the compounds of Formula II(b) are protected prior to reaction with the reagents of Formula III. In an embodiment, the protected form of the compounds of Formula II(b) is a ketal of Formula IV:

wherein

⁓ represents a single or double bond;

$R^2$ is selected from H, $C_{1-10}$alkyl, $C_{1-10}$acyl, $C_{6-10}$aryl, $C_{3-10}$cycloalkyl, $C_{1-10}$alkylene$C_{6-10}$aryl and $C_{1-10}$alkylene$C_{3-10}$cycloalkyl; and $R^4$ and $R^5$ are each independently the same or different hydrolysable protecting group, or $R^4$ and $R^5$, together with the oxygen atom to which each is bonded, form a hydrolysable cyclic protecting group; and wherein one or more available hydrogens in $R^2$, $R^4$ and $R^5$ is/are optionally replaced with F and/or one or more of available atoms in $R^2$, $R^4$ and $R^5$ is/are optionally replaced with an isotopic label.

The compounds of Formula IV are prepared by reacting a compound of Formula II(b) under conditions to provide the compounds of Formula IV. In an embodiment, the conditions to provide the compounds of Formula IV comprise adding a suitable ketone activating reagent, for example TMSCl to a stirred suspension or solution of the compound of Formula II(b) and a suitable alcohol, for example, methanol or ethylene glycol, optionally in a suitable solvent, for example, $CH_2Cl_2$, and allowing the mixture to stir for a time and temperature for the conversion of the compound of Formula II(b) to the compound of Formula IV to proceed to a sufficient extent, for example at about −10° C. to about 50° C., about 0° C. to about 25° C. or about room temperature for about 30 minutes to about 10 hours, about 2 hours to about 6 hours, or about 2 hours. In this embodiment, TLC monitoring of the reaction mixture using a suitable solvent mixture, for example $CHCl_3$/MeOH/$NH_4$OH in a ratio of, for example, about 5:1:0.01 as eluent can be optionally used to indicate the reaction is complete.

In an embodiment of the application, the suitable alcohol is a monofunctional alcohol. It is an embodiment that the monofunctional alcohol is methanol. In this embodiment, both $R^4$ and $R^5$ are Me. In another embodiment, the suitable alcohol is a difunctional alcohol. It is an embodiment that the difunctional alcohol is ethylene glycol. In this embodiment, $R^4$ and $R^5$, together with the oxygen atom to which each is bonded, and the carbon atom to which each oxygen atom is bonded, form a dioxolane moiety.

Reaction of the compounds of Formula IV with the reagents of Formula III provides compounds of Formula V:

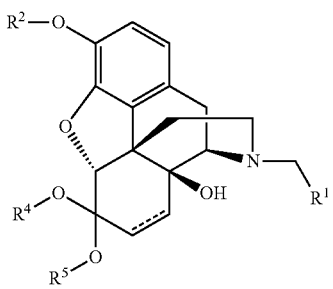

V wherein

⌇⌇⌇ represents a single or double bond;

$R^1$ is selected from $C_{1-10}$alkyl, $C_{2-10}$alkenyl, $C_{3-10}$cycloalkyl, $C_{3-10}$cycloalkenyl, $C_{6-10}$aryl, $C_{1-10}$alkylene$C_{6-10}$aryl and $C_{1-10}$alkylene$C_{3-10}$cycloalkyl;

$R^2$ is selected from H, $C_{1-10}$alkyl, $C_{1-10}$acyl, $C_{6-10}$aryl, $C_{3-10}$cycloalkyl, $C_{1-10}$alkylene$C_{6-10}$aryl and $C_{1-10}$alkylene$C_{3-10}$cycloalkyl; and $R^4$ and $R^5$ are each independently the same or different hydrolysable protecting group, or $R^4$ and $R^5$, together with the oxygen atom to which each is bonded, form a hydrolysable cyclic protecting group; and wherein one or more available hydrogens in $R^1$, $R^2$, $R^4$ and $R^5$ is/are optionally replaced with F and/or one or more of available atoms in $R^1$, $R^2$, $R^4$ and $R^5$ is/are optionally replaced with an isotopic label.

Deprotection of the compounds of Formula V under hydrolysis conditions provides ketones of Formula I(b):

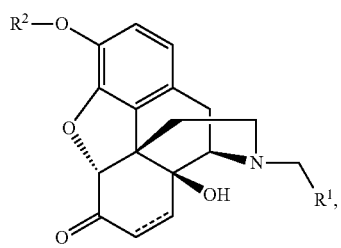

I(b)

wherein

⌇⌇⌇ represents a single or double bond;

$R^1$ is selected from $C_{1-10}$alkyl, $C_{2-10}$alkenyl, $C_{3-10}$cycloalkyl, $C_{3-10}$cycloalkenyl, $C_{6-10}$aryl, $C_{1-10}$alkylene$C_{6-10}$aryl and $C_{1-10}$alkylene$C_{3-10}$cycloalkyl;

$R^2$ is selected from H, $C_{1-10}$alkyl, $C_{1-10}$acyl, $C_{6-10}$aryl, $C_{3-10}$cycloalkyl, $C_{1-10}$alkylene$C_{6-10}$aryl and $C_{1-10}$alkylene$C_{3-10}$cycloalkyl; and wherein one or more available hydrogens in $R^1$ and $R^2$ is/are optionally replaced with F and/or one or more of available atoms in $R^1$ and $R^2$ is/are optionally replaced with an isotopic label.

In this embodiment, it is possible to prepare the known morphine analogs, naloxone I(b)(i), naltrexone I(b)(ii) and nalbuphone I(b)(iii):

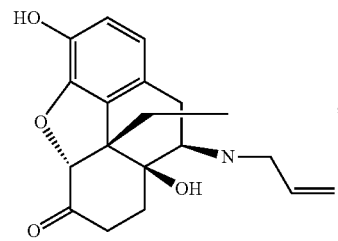

I(b)(i)

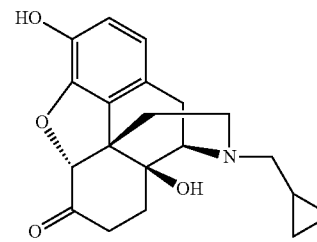

I(b)(ii)

and

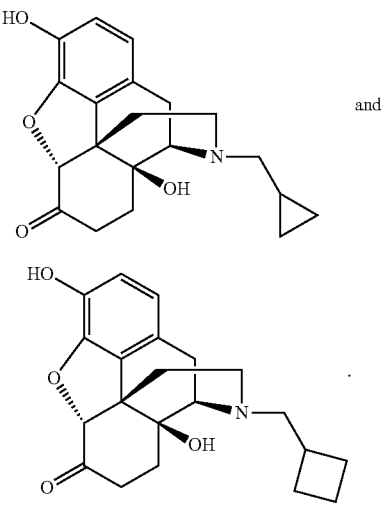

I(b)(iii)

In an embodiment, the hydrolysis conditions to provide the compounds of Formula I(b) comprise treating the compounds of Formula V under suitable acidic conditions for a time and temperature for the conversion of the compounds of Formula V to the compounds of Formula I(b) to proceed to a sufficient extent, for example at a temperature of about 25° C. to about 100° C., about 60° C. to about 80° C., or about 60° C. for about 30 minutes to about 8 hours, about 2 hours to about 4 hours, or about 2 hours. It is an embodiment that the suitable acidic conditions comprise adding a suitable acid, for example, about 2 N to about 6 N HCl to a stirred solution of the compound of Formula V in a suitable organic solvent, for example, THF or acetone.

In a further embodiment of the application, prior to reaction with the reagents of Formula III, the compounds of Formula II(b) are treated under reducing conditions to provide compounds of Formula II(a):

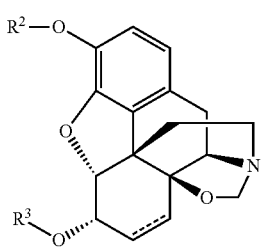

II(a)

wherein

⌇⌇⌇ represents a single or double bond;

$R^2$ is selected from H, $C_{1-10}$alkyl, $C_{1-10}$acyl, $C_{6-10}$aryl, $C_{3-10}$cycloalkyl, $C_{1-10}$alkylene$C_{6-10}$aryl and $C_{1-10}$alkylene$C_{3-10}$cycloalkyl;

$R^3$ is H; and wherein one or more available hydrogens in $R^2$ is/are optionally replaced with F and/or one or more of available atoms in $R^2$ and $R^3$ is/are optionally replaced with an isotopic label.

The compounds of Formula II(a), wherein $R^3$=H are available by treating compounds of Formula II(b) under reducing conditions. In an embodiment, the reducing conditions to provide the compounds of Formula II(a) wherein $R^3$ is H comprise treating the compounds of Formula II(b) in a suitable solvent, for example, methanol with a suitable reducing agent, for example metal hydride reducing agents, for example, $NaBH_4$ for a time and temperature for the conversion of the compounds of Formula II(b) to the compounds of Formula II(a), wherein $R^3$ is H to proceed to a sufficient extent, for example at about 0° C. to about 30° C., or about room temperature for about 0.5 hours to about 2 hours, or about 1 hour.

Reaction of the compounds of Formula II(a), wherein $R^3$ is H with the reagents of Formula III provides compounds of Formula I(a):

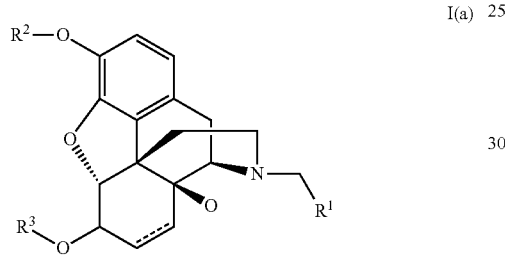

wherein

⋯ represents a single or double bond;

$R^1$ is selected from $C_{1-10}$alkyl, $C_{2-10}$alkenyl, $C_{3-10}$cycloalkyl, $C_{3-10}$cycloalkenyl, $C_{6-10}$aryl, $C_{1-10}$alkylene$C_{6-10}$aryl and $C_{1-10}$alkylene$C_{3-10}$cycloalkyl;

$R^2$ is selected from H, $C_{1-10}$alkyl, $C_{1-10}$acyl, $C_{6-10}$aryl, $C_{3-10}$cycloalkyl, $C_{1-10}$alkylene$C_{6-10}$aryl and $C_{1-10}$alkylene$C_{3-10}$cycloalkyl;

$R^3$ is H; and wherein one or more available hydrogens in $R^1$ and $R^2$ is/are optionally replaced with F and/or one or more of available atoms in $R^1$, $R^2$ and $R^3$ is/are optionally replaced with an isotopic label.

In this embodiment, it is possible to prepare the known morphine analog nalbuphine I(a)(iii):

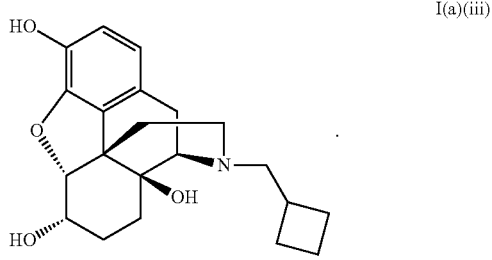 [SMILES: Oc1ccc2c3c1O[C@H]1[C@@H](O)CC[C@@]4(O)[C@@H](C2)N(CC2CCC2)CC[C@]314]

It is a further embodiment of the application that morphine analogs of Formula I can be prepared from the oxazolidines of Formula II in a one-pot synthesis without the isolation of intermediates.

The processes of the present application may be performed using continuous or batch processes. For commercial scale preparations, continuous processes are suitable. Methods of performing chemical processes in continuous or batch modes are known in the art. When continuous processes are used, the reaction temperature and/or pressure may be higher than those used in batch processes.

The following non-limiting examples are illustrative of the present application:

EXAMPLES

Example 1

(5aR,6R,8aS,11aR,11bS)-2-acetoxy-5,5a,9,10-tetrahydro-11,11-dimethoxy,6,11b-Ethano-7H-furo[2',3',4',5':4,5]phenanthro[9,8a-d]-oxazole

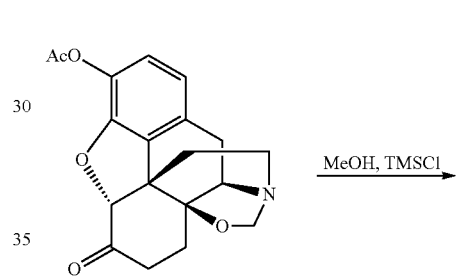

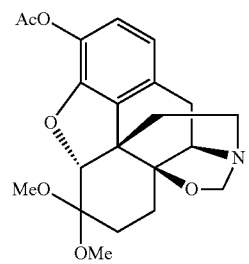

To a stirred suspension of the oxazolidine of Formula II(b) ($R^2$=Ac, ⋯ represents a single bond; 60 mg, 0.18 mmol) in MeOH (5 mL) was added TMSCl (0.50 mL). After the addition of TMSCl, a homogenous yellowish solution was observed. The mixture was allowed to stir at room temperature for 2 h, at which time TLC monitoring of the reaction mixture using $CHCl_3$/MeOH/$NH_4$OH (5:1:0.01) as eluent indicated the reaction was complete. The reaction mixture was diluted with dichloromethane (10 mL) and the resulting solution was washed with saturated $NaHCO_3$ (5 mL). The organic layer was dried with $MgSO_4$, filtered and evaporated to dryness via rotary evaporation to afford 50 mg (82%) of a compound of Formula IV(a) ($R^2$=Ac, $R^4$ and $R^5$=Me, ⋯ represents a single bond) as an oil which was used in the next step without further purification.

Example 2

General Procedure for Grignard Reactions of Ketal IV(a)

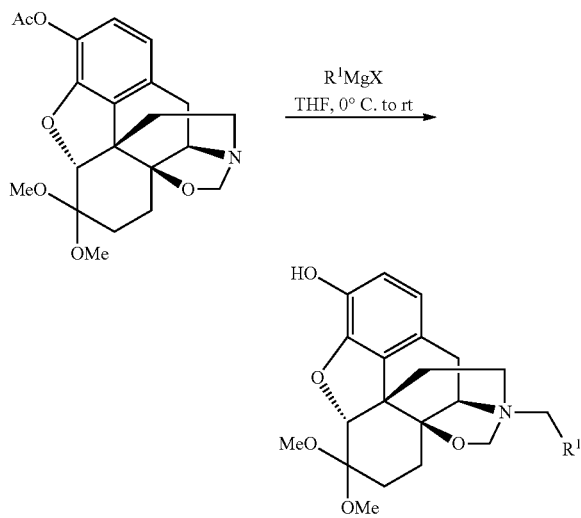

To a stirred solution of the oxazolidine of Formula IV(a) from Example 1 (1 mmol) in THF (10 mL) at 0° C. was added a reagent of Formula III wherein A is MgX; III(i) (R$^1$=vinyl, X=Br); III(ii) (R$^1$=cyclopropyl, X=Br); or III(iv) (R$^1$=cyclobutyl, X=Cl) (5 mmol) dropwise. The mixture was allowed to warm up to room temperature and stirred for a further 2 h, then it was quenched with saturated NH$_4$Cl solution (10 mL) and was diluted with EtOAc (10 mL). The layers were separated and the aqueous layer was extracted further with EtOAc (2×10 mL). The combined organic extracts were dried over MgSO$_4$, filtered and concentrated using rotary evaporation to afford crude compounds of Formula V. Chromatography on silica gel using mixtures of CH$_2$Cl$_2$ and MeOH afforded compounds of Formula V(a)(i), V(a)(ii) and V(a)(iii) as white solids (56-83% yield).

(a) 17-allyl-4,5α-epoxy-3,14-dihydroxy-6,6-dimethoxymorphinan, V(a)(i)

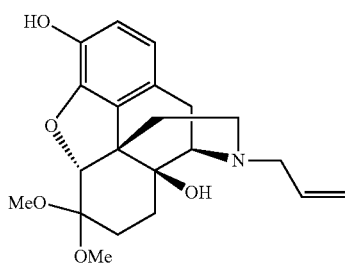 [SMILES: C=CCN1CC[C@]23c4c5ccc(O)c4O[C@H]2C(OC)(OC)CC[C@@]3(O)[C@H]1C5]

83% yield. [α]$_D^{20}$ −92.3 (c=0.8, CHCl$_3$); R$_f$=0.26 (7:2; CH$_2$Cl$_2$/MeOH); IR(CHCl$_3$) ν 3435, 2957, 2834, 1642, 1458, 1333, 1141, 1110, 1047, 989, 908, 732 cm$^{-1}$; $^1$H NMR (300 MHz, CDCl$_3$) δ 6.71 (d, J=8.1 Hz, 1H), 6.55 (d, J=8.1 Hz, 1H), 5.77-5.86 (m, 1H), 5.21 (d, J=18.0 Hz, 1H), 4.60 (s, 1H), 3.38 (s, 3H), 3.03-3.11 (m, 2H), 3.12 (s, 3H), 3.03 (s, 1H), 2.94 (d, J=5.7 Hz, 1H), 2.62 (d, J=5.7 Hz, 1H), 2.53-2.57 (m, 1H), 2.31 (ddd, J=12.3, 12.0, 3.0 Hz, 1H), 2.19 (ddd, J=12.3, 12.0, 3.0 Hz, 1H), 1.87-1.96 (m, 1H), 1.40-1.59 (m, 5H); $^{13}$C NMR (75 MHz, CDCl$_3$) δ 144.8, 137.7, 135.4, 130.8, 124.5, 118.4, 117.8, 116.8, 99.8, 91.8, 69.9, 62.7, 57.7, 49.1, 48.2, 48.1, 43.6, 31.9, 27.9, 24.6, 22.5; MS (EI+) m/z (%) 373(5), 358 (10), 342(28), 341(100), 326(12), 139(12), 101(14), 57(21), 56(20), 43(25); HRMS (EI+) calcd for C$_{21}$H$_{27}$NO$_5$ 373.1889. found 373.1891.

(b) 17-cyclopropylmethyl-4,5α-epoxy-3,14-dihydroxy-6,6-dimethoxymorphinan, V(a)(ii)

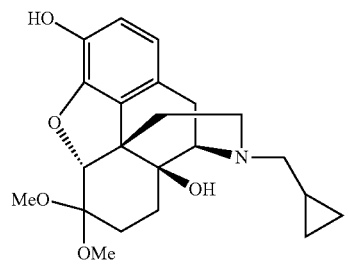 [SMILES: COC1(OC)CC[C@@]2(O)[C@H]3Cc4ccc(O)c5c4[C@@]2(CCN3CC2CC2)[C@H]1O5]

67% yield. $^1$H NMR (300 MHz, CDCl$_3$) δ 6.68 (d, J=8.1 Hz, 1H), 6.51 (d, J=8.1 Hz, 1H), 5.40 (s, 1H), 4.58 (s, 1H), 3.36 (s, 3H), 3.10 (s, 4H), 2.99 (d, J=18.2 Hz, 1H), 2.50-2.70 (m, 2H), 2.35 (m, 2H), 2.22-2.31 (m, 1H), 2.06-2.22 (m, 1H), 1.83-1.96 (m, 1H), 1.34-1.60 (m, 4H), 0.75-0.92 (m, 1H), 0.42-0.60 (m, 1H), 0.08-0.20 (m, 2H).

(c) 17-cyclobutylmethyl-4,5α-epoxy-3,14-dihydroxy-6,6-dimethoxymorphinan, V(a)(iii)

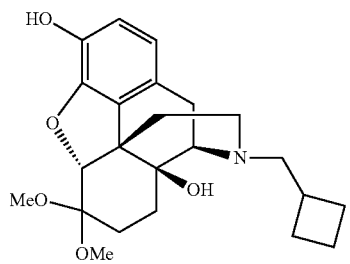 [SMILES: COC1(OC)CC[C@@]2(O)[C@H]3Cc4ccc(O)c5c4[C@@]2(CCN3CC2CCC2)[C@H]1O5]

56% yield. [α]$_D^{20}$ −110.5 (c=1.0, CH$_2$Cl$_2$); R$_f$=0.37 (10:1; CH$_2$Cl$_2$/MeOH); IR(CHCl$_3$) ν 3399, 2929, 2832, 2854, 1642, 1621, 1504, 1456, 1330, 1239, 1141, 1049, 988, 751 cm$^{-1}$; $^1$H NMR (300 MHz, CDCl$_3$) δ 6.70 (d, J=8.1 Hz, 1H), 6.53 (d, J=8.1 Hz, 1H), 4.56 (s, 1H), 3.37 (s, 3H), 3.13 (s, 3H), 3.05 (d, J=18.3 Hz, 1H), 2.84 (d, J=5.7 Hz, 1H), 2.60 (dd, J=18.3, 6.0 Hz, 1H), 2.46-2.55 (m, 4H), 2.20-2.30 (m, 2H), 2.04-2.09 (m, 2H), 1.84-1.96 (m, 2H), 1.65-1.70 (m, 2H), 1.38-1.45 (m, 5H); $^{13}$C NMR (75 MHz, CDCl$_3$) δ 144.8, 137.7, 130.8, 124.5, 118.4, 117.0, 99.7, 91.5, 69.7, 60.5, 49.01, 48.2, 48.1, 44.0, 33.7, 32.1, 28.0, 27.0, 26.7, 24.5, 22.8, 18.7; MS (EI+) m/z (%) 401(9), 315(20), 314(100), 139(11), 97(12), 89(31), 71(59), 55(46), 43(94); HRMS (EI+) calcd for C$_{23}$H$_{31}$NO$_5$ 401.2202. found 401.2203.

Example 3

General Procedure for the Hydrolysis of V(a)(i)-V(a)(iii)

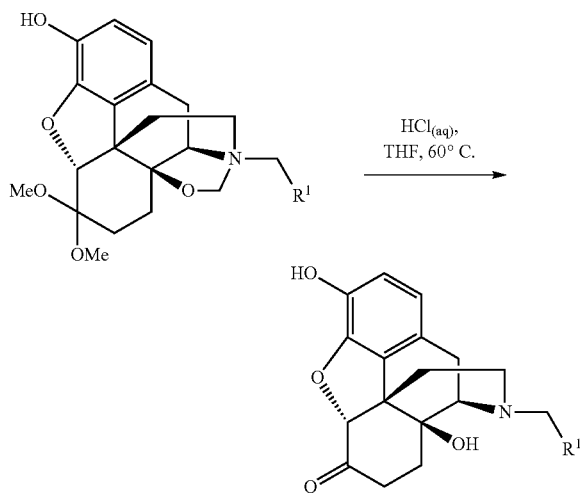

To a stirred solution of a compound of Formula V from Example 2 (0.10 mmol) in THF (2 mL) was added 3 N HCl (1 mL). The resulting solution was heated to 60° C. for 2 h. The mixture was concentrated via rotary evaporation to remove THF. A saturated solution of NaHCO$_3$ was added to adjust the pH of the mixture to 8. It then was extracted with CH$_2$Cl$_2$ (3×5 mL). The combined organic extracts were dried, filtered and concentrated via rotary evaporation to afford naloxone, naltrexone or nalbuphone as white solids (76-87% yield).

(a) Naloxone, I(b)(i)

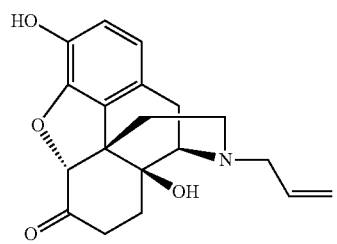 [SMILES: C=CCN1CC[C@]23c4c5ccc(O)c4O[C@H]2C(=O)CC[C@@]3(O)[C@H]1C5]

81% yield. mp 179-180° C. (EtOAc/hexanes); lit.[7] 179.5° C. (toluene).

(b) Naltrexone, I(b)(ii)

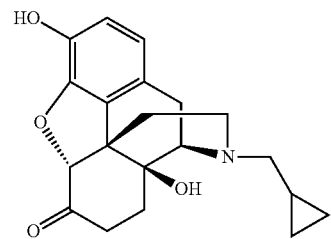 [SMILES: O=C1CC[C@@]2(O)[C@H]3Cc4ccc(O)c5c4[C@@]2(CCN3CC2CC2)[C@H]1O5]

76% yield. mp 164-165° C. (CH$_2$Cl$_2$/hexanes); lit.[8] 167-169° C., (CH$_2$Cl$_2$).

(c) Nalbuphone, I(b)(iii)

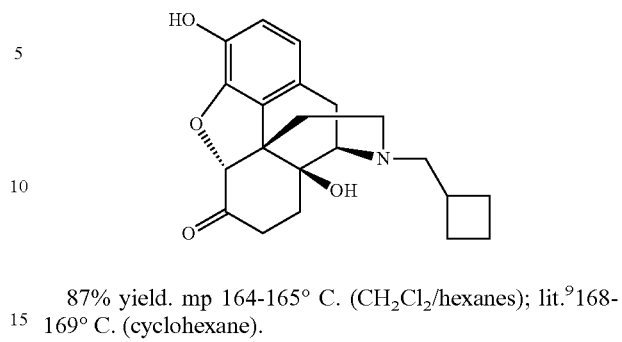

87% yield. mp 164-165° C. (CH$_2$Cl$_2$/hexanes); lit.[9] 168-169° C. (cyclohexane).

Example 4

One-Pot Preparation of Naloxone

To a stirred suspension of the oxazolidine of Formula II(b) (R$^2$=Ac, ⚌ represents a single bond; 100 mg, 0.293 mmol) in MeOH (5 mL) was added TMSCl (0.5 mL). The reaction mixture was stirred for 2 h at room temperature. All the volatiles were removed using rotary evaporation and further drying in vacuum. The resulting yellow oil was cooled to 0° C. and to it was added dropwise 1 M vinylmagnesium bromide (2 mL). The resulting mixture was allowed to warm up to room temperature and stirred for another 2 h. The pH of the reaction mixture was adjusted to 1.5 using 6 N HCl. A 1:1 mixture of THF/H$_2$O (2 mL) was added to clarify the cloudy solution. The resulting clear solution was heated to 60° C. for 2 h. The cooled reaction mixture was concentrated via rotary evaporation to remove THF. The pH was adjusted to 8 using saturated NaHCO$_3$ solution and was extracted with EtOAc (3×15 mL). The combined EtOAc extracts were dried over MgSO$_4$, filtered and concentrated to afford a crude residue that was chromatographed on silica gel using CH$_2$Cl$_2$/MeOH (10:1) as eluent to afford Naloxone I(b)(i) (72 mg, 75% yield).

Example 5

Preparation of Nalbuphine, I(a)(iii)

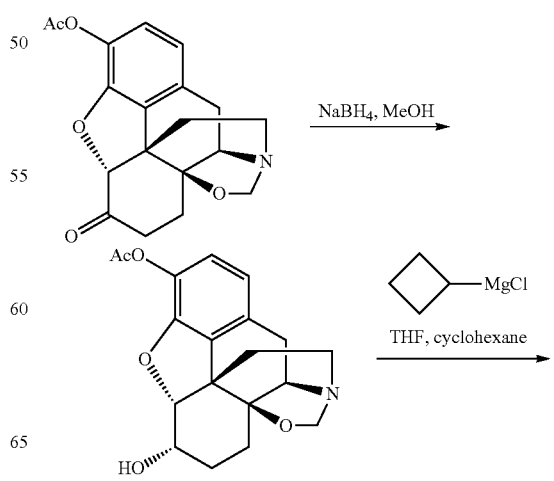

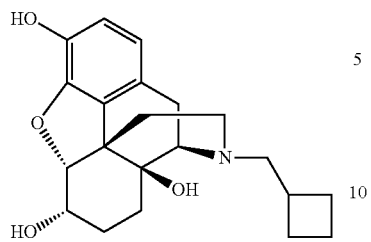

To a stirred solution of the oxazolidine of Formula II(b) (R²=Ac, ⋯ represents a single bond; 50 mg, 0.15 mmol) in MeOH (1 mL) was added NaBH₄ (8 mg, 0.22 mmol). The solution was stirred at room temperature for 1 h. Acetone (1 mL) was added and the resulting mixture was concentrated using rotary evaporation. The crude residue was diluted with diethyl ether (10 mL) and was washed with water (3 mL). The organic layer was separated and the aqueous was further extracted with EtOAc (2×5 mL). The combined organic extracts were dried over MgSO₄, filtered and evaporated to afford the intermediate alcohol of Formula II(a) (R²=Ac, R³=H, ⋯ represents a single bond; 40 mg) which was used as crude in the next step. To a stirred solution of this crude intermediate alcohol (40 mg, 0.12 mmol) in THF at 0° C. was added cyclobutylmagnesium chloride (60 mmol). The resulting solution was stirred at room temperature for 2 h. The reaction mixture was quenched with saturated NH₄Cl solution (3 mL). The resulting suspension was extracted with EtOAc (3×10 mL). The combined organic extracts were dried over MgSO₄, filtered and concentrated using rotary evaporation. The crude residue was chromatographed on silica gel using CH₂Cl₂/MeOH as eluent to afford nalbuphine I(a)(iii) as a solid (21 mg, 40% yield).

¹H NMR (300 MHz, DMSO) δ 8.81 (s, 1H), 6.55 (d, J=8.0 Hz, 1H), 6.42 (d, J=8.0 Hz, 1H), 4.75 (s, 1H), 4.43 (d, J=5.6 Hz, 1H), 4.38 (d, J=4.5 Hz, 1H), 4.00 (m, 1H), 2.96 (d, J=18.4 Hz, 1H), 2.75 (m, 1H), 2.50-2.53 (m, 2H), 2.39-2.45 (m, 2H), 2.10 (m, 2H), 1.85 (m, 2H), 1.81 (m, 1H), 1.63 (m, 2H), 1.45 (m, 2H), 1.31 (m, 2H), 0.97 (m, 1H).

Example 6

(5aR,6R,8aS,11aR,11bS)-2-acetoxy-5,5a,9,10-tetrahydro-11(11aH)-spiro-2-(1,3-dioxolan)-,6,11b-Ethano-7H-furo[2',3',4',5':4,5]-phenanthro[9,8a-d]oxazole

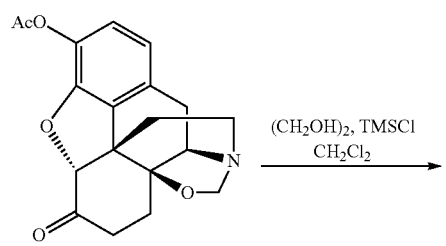

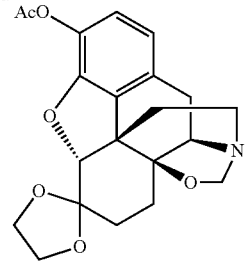

To a stirred solution of the oxazolidine of Formula II(b) (R²=Ac, ⋯ represents a single bond; 650 mg, 2.16 mmol) and ethylene glycol (14.3 mL, 260 mmol) in CH₂Cl₂ (15 mL) was added TMSCl (1.46 mL, 11.0 mmol). The mixture was allowed to stir at room temperature for 2 h, at the end of which TLC monitoring of the reaction mixture using CHCl₃/MeOH/NH₄OH (5:1:0.01) as eluent indicated the reaction was complete. The reaction mixture was diluted with dichloromethane (30 mL) and the resulting solution was carefully washed with saturated NaHCO₃ (15 mL). The organic layer was dried with MgSO₄, filtered and evaporated to dryness via rotary evaporation to afford the ketal of Formula IV(b) (437 mg, 67%) as an oil which was used in the next step without further purification.

Example 7

General Procedure for Grignard Reactions of Ketal IV(b)

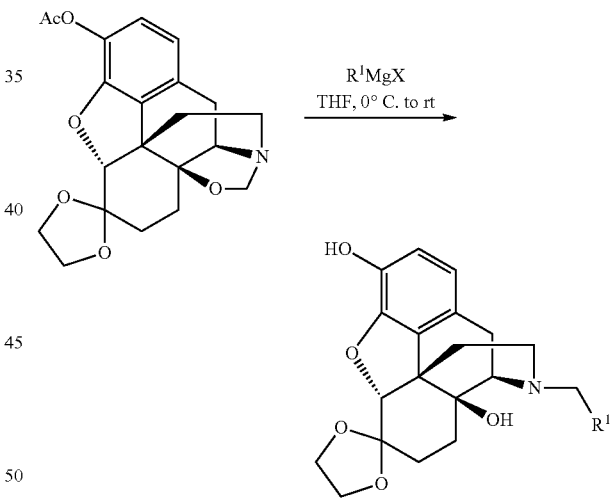

To a stirred solution of the oxazolidine of Formula IV(b) from Example 6 (1 mmol) in THF (10 mL) at 0° C. was added a reagent of Formula III wherein A is MgX; III(i) (R¹=vinyl, X=Br); III(ii) (R¹=cyclopropyl, X=Br); or III(iv) (R¹=cyclobutyl, X=Cl) (5 mmol) dropwise. The mixture was allowed to warm up to room temperature and stirred for a further 2 h, then it was quenched with saturated NH₄Cl solution (10 mL) and was diluted with EtOAc (10 mL). The layers were separated and the aqueous was extracted further with EtOAc (2×10 mL). The combined organic extracts were dried over MgSO₄, filtered and concentrated using rotary evaporation to afford crude compounds of Formula V. Chromatography on silica gel using mixtures of CH₂Cl₂ and MeOH afforded compounds of Formulas V(b)(i)-V(b)(iii) as white solids (46-70% yield).

(a) 4,5α-epoxy-3,14β-dihydroxy-17-(prop-2-enyl)-morphinane-6-spiro-2'-(1,3-dioxolan), V(b)(i)

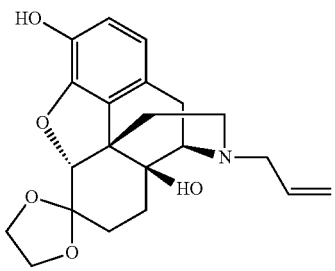 [SMILES: C=CCN1CC[C@]23c4c5ccc(O)c4O[C@H]2C2(CC[C@@]3(O)[C@H]1C5)OCCO2]

46% yield. ¹H NMR (600 MHz, CDCl₃) δ 6.72 (d, J=8.1 Hz, 1H), 6.58 (d, J=8.1 Hz, 1H), 5.78-5.84 (m, 1H), 5.14-5.23 (m, 2H), 4.60 (s, 1H), 4.12-4.18 (m, 1H), 3.84-3.99 (m, 4H), 3.15 (d, J=6.0 Hz, 13H), 3.06 (d, J=18.6 Hz, 1H), 2.93 (s, 1H), 2.53-2.62 (m, 2H), 2.15-2.29 (m, 3H), 1.53-1.57 (m, 3H), 1.43 (d, J=12.6 Hz, 2H); MS (EI+) m/z (%) 371(100), 358 (10), 330(22), 289(32), 272(45), 242(27), 99(94), 82(50), 70(39), 55(31); HRMS (EI+) calcd for $C_{21}H_{25}NO_5$ 371.1733. found 371.1734.

(b) 17-cyclopropylmethyl-4,5α-epoxy-3,14β-dihydroxy-morphinane-6-spiro-2-(1,3-dioxolan), V(b)(ii)

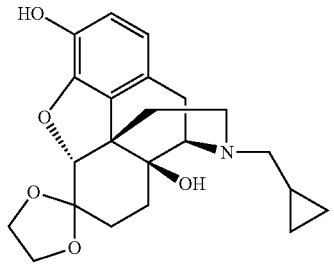 [SMILES: Oc1ccc2c3c1O[C@H]1C4(CC[C@@]5(O)[C@@H](C2)N(CC2CC2)CC[C@]315)OCCO4]

70% yield. ¹H NMR (300 MHz, CDCl₃) δ 6.72 (d, J=8.1 Hz, 1H), 6.56 (d, J=8.1 Hz, 1H), 4.61 (s, 1H), 4.16-4.19 (m, 1H), 3.83-3.98 (m, 4H), 3.03 (d, J=18.3 Hz, 1H), 2.55-2.66 (m, 2H), 2.28-2.42 (m, 3H), 2.16-2.23 (m, 3H), 1.48-1.68 (m, 5H), 0.85-0.87 (m, 1H), 0.54-0.56 (m, 2H), 0.15-0.16 (m, 2H); MS (EI+) m/z (%) 385(100), 344(22), 330(12), 288(14), 256(16), 110(31), 99(62).

(c) 17-cyclobutylmethyl-4,5α-epoxy-3,14β-dihydroxy-morphinane-6-spiro-2-(1,3-dioxolan), V(b)(iii)

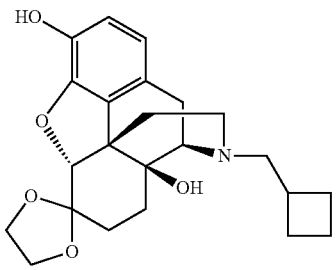 [SMILES: Oc1ccc2c3c1O[C@H]1C4(CC[C@@]5(O)[C@@H](C2)N(CC2CCC2)CC[C@]315)OCCO4]

49% yield. $[α]_D^{20}$ −51.2 (c=1.0, CHCl₃); IR(CHCl₃) ν 3417, 2957, 1642, 1502, 1456, 1324, 1157, 1035, 799, 752 cm⁻¹; ¹H NMR (300 MHz, CDCl₃) δ 6.72 (d, J=8.1 Hz, 1H), 6.57 (d, J=8.1 Hz, 1H), 4.59 (s, 1H), 4.15-4.18 (m, 1H), 3.82-3.87 (m, 5H), 3.06 (d, J=18.3 Hz, 1H), 2.86 (d, J=5.7, 1H), 2.61 (dd, J=18.3, 5.7 Hz, 1H), 2.49-2.59 (m, 4H), 2.17-2.28 (m, 2H), 2.06-2.17 (m, 3H), 1.86-1.94 (m, 2H), 1.66-1.71 (m, 2H), 1.53-1.57 (m, 3H), 1.41-1.45 (m, 1H); MS (EI+) m/z (%) 399(12), 315(20), 344(100), 243(11), 139(9), 99(14), 86(39), 84(76), 60(10), 43(31); HRMS (EI+) calcd for $C_{23}H_{29}NO_5$ 399.2046. found 399.2043.

Example 8

General Procedure for the Hydrolysis of V(b)(i)-V(b)(iii)

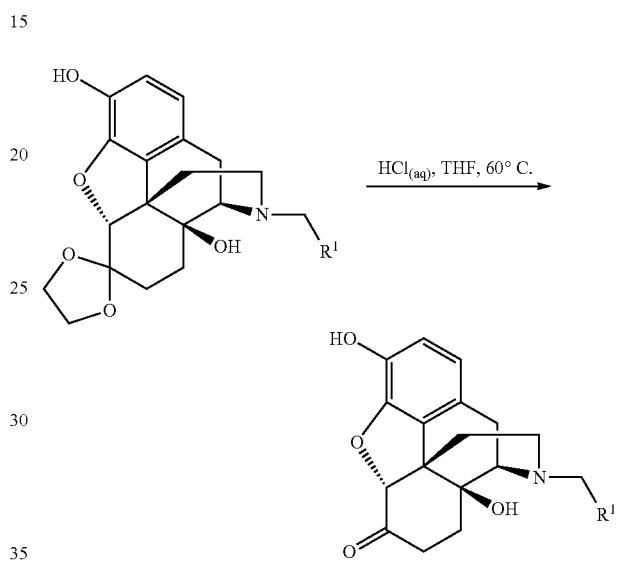

To a stirred solution of a compound of Formula V from Example 7 (0.10 mmol) in acetone (2 mL) was added 6 N HCl (0.5 mL). The resulting solution was heated to 60° C. for 2 h. The mixture was concentrated via rotary evaporation to remove acetone. A saturated solution of NaHCO₃ was added to adjust the pH of the mixture to 8. It was then extracted with CH₂Cl₂ (3×5 mL). The combined organic extracts were dried, filtered and concentrated via rotary evaporation to afford naloxone I(b)(i), naltrexone I(b)(ii) and nalbuphone I(b)(iii) as white solids, with yields of 63%, 71%, and 78%, respectively.

While the present application has been described with reference to what are presently considered to be the preferred examples, it is to be understood that the application is not limited to the disclosed examples. To the contrary, the application is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

FULL CITATIONS FOR DOCUMENTS REFERRED TO IN THE SPECIFICATION

[1] Processes for the preparation of morphinane and morphinone compounds. Hudlicky, T.; Carroll, R.; Leisch, H.;

Machara, A.; Werner, L.; Adams, D. R. PCT Int. Appl. PCT/CA2010/000587 (2010), 102 pp. CODEN: PIXXD2 WO 2010121369 A1 20101028 CAN 153:555396 AN 2010:1342585.

[2] Synthesis of nalbuphine from oripavine via N-demethylation of N-cyclobutylmethyl oripavine. Machara, A.; Cox, D. P.; Hudlicky, T. *Heterocycles,* 2012, 84, 615-623.

[3] L. Werner, A. Machara, D. R. Adams, D. P. Cox, T. Hudlicky, *J. Org. Chem.* 2011, 76, 4628.

[4] Process for the Preparation of Morphine Analogs via Metal Catalyzed N-Demethylation/Functionalization and Intramolecular Group Transfer. Hudlicky, T.; Machara, A. US Patent Application Publication No. 2012/0283444.

[5] Processes and Intermediates in the Preparation of Morphine Analogs via N-Demethylation of N-Oxides Using Cyclodehydration Reagents. Hudlicky, T.; Machara, A.; Werner, L.; Wernerova, M.; Endoma-Arias, M. A. US Patent Application Publication No. 2012/0283443; PCT Publication No. WO/2012/149633.

[6] Edward M. Burgess, Harold R. Penton Jr., and E. A. Taylor. "Thermal reactions of alkyl N-carbomethoxysulfamate esters". *J. Org. Chem.* 1973, 38(1):26-31.

[7] Andre, J.-D.; Dormoy, J.-R.; Heymes, A. *Synth. Comm.,* 1992, 22, 2313.

[8] Pillai, O.; Hamad, M. O.; Crooks, P. A.; Stinchcomb, A. L. *Pharm. Res.,* 2004, 21, 1146.

[9] Hudlicky, T.; Carroll, R.; Leisch, H.; Machara, A.; Werner, L.; Adams, D. R. PCT Publication No. WO/2010/121369 A1.

We claim:

1. A process for the preparation of a compound of Formula I:

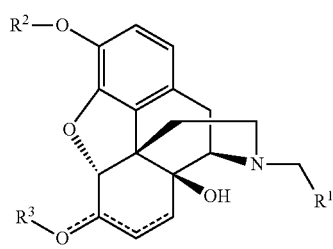

I wherein

≈≈≈ represents a single or double bond, provided that two double bonds are not adjacent to each other;

$R^1$ is selected from $C_{3-10}$cycloalkyl, $C_{3-10}$cycloalkenyl, $C_{1-10}$alkyl, $C_{2-10}$alkenyl, $C_{6-10}$aryl, $C_{1-10}$alkylene$C_{6-10}$aryl and $C_{1-10}$alkylene$C_{3-10}$cycloalkyl; and $R^2$ and $R^3$ are independently selected from H, $C_{1-10}$alkyl, $C_{1-10}$acyl, $C_{6-10}$aryl, $C_{3-10}$cycloalkyl, $C_{1-10}$alkylene$C_{6-10}$ aryl and $C_{1-10}$alkylene$C_{3-10}$cycloalkyl, except when ≈≈≈ O represents =O, then $R^3$ is not present;

the process comprising:

(a) reacting a compound of Formula II or a protected form thereof:

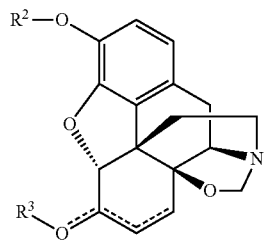

II wherein

≈≈≈ represents a single or double bond, provided that two double bonds are not adjacent to each other; and $R^2$ and $R^3$ are independently selected from H, $C_{1-10}$alkyl, $C_{1-10}$acryl, $C_{6-10}$aryl, $C_{3-10}$cycloalkyl, $C_{1-10}$alkylene $C_{6-10}$aryl and $C_{1-10}$alkylene$C_{3-10}$cycloalkyl, except when ≈≈≈ O represents =O, then $R^3$ is not present;

with a reagent of Formula III:

$$R^1 A \quad \quad III,$$

wherein $R^1$ is selected from $C_{1-10}$alkyl, $C_{2-10}$alkenyl, $C_{3-10}$cycloalkyl, $C_{3-10}$cycloalkenyl, $C_{6-10}$aryl, $C_{1-10}$alkylene$C_{6-10}$aryl and $C_{1-10}$alkylene$C_{3-10}$cycloalkyl; and A is a suitable metallic or organometallic countercation; and (b) optionally deprotecting the compound derived from reacting the compound of Formula II or protected form thereof with the reagent of Formula III;

under conditions to provide a compound of Formula I;

wherein in the compounds of Formulae I, II and III one or more available hydrogens in $R^1$, $R^2$ and $R^3$ is/are optionally replaced with F and/or one or more of available atoms in $R^1$, $R^2$ and $R^3$ is/are optionally replaced with an isotopic label.

2. The process of claim 1, wherein the compound of Formula I is selected from a compound of Formula I(a), I(b) and I(c):

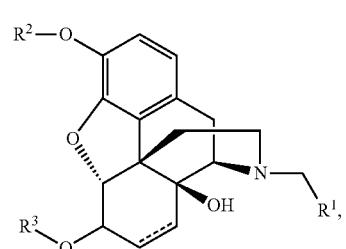

I(a)

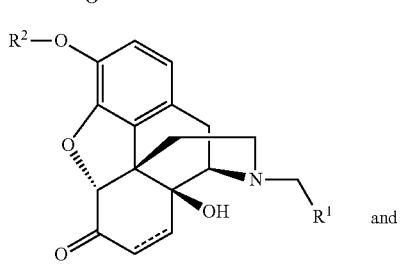

I(b)

and

-continued

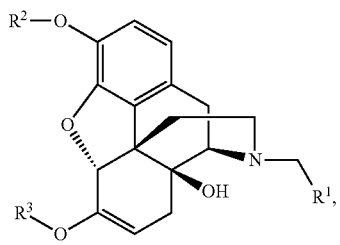
I(c)

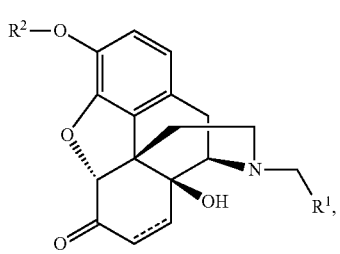
I(b)

wherein

≈ represents a single or double bond;

$R^1$ is selected from $C_{1-10}$alkyl, $C_{2-10}$alkenyl, $C_{3-10}$cycloalkyl, $C_{3-10}$cycloalkenyl, $C_{6-10}$aryl, $C_{1-10}$alkylene$C_{6-10}$aryl and $C_{1-10}$alkylene$C_{3-10}$cycloalkyl; and $R^2$ and $R^3$ are independently selected from H, $C_{1-10}$alkyl, $C_{1-10}$acyl, $C_{6-10}$aryl, $C_{3-10}$cycloalkyl, $C_{1-10}$alkylene$C_{6-10}$aryl and $C_{1-10}$alkylene$C_{3-10}$cycloalkyl; and the compound of Formula II is selected from a compound of Formula II(a), II(b) and II(c):

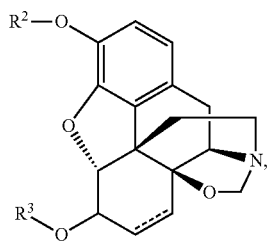
II(a)

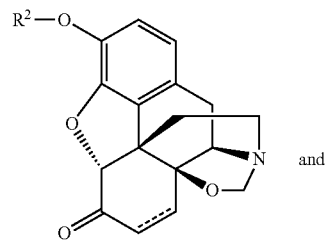
II(b)

and

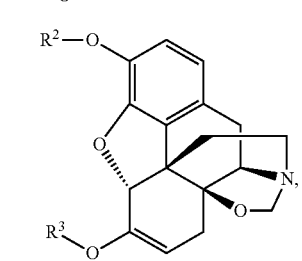
II(c)

wherein

≈ represents a single or double bond; and $R^2$ and $R^3$ are independently selected from H, $C_{1-10}$alkyl, $C_{1-10}$acyl, $C_{6-10}$aryl, $C_{3-10}$cycloalkyl, $C_{1-10}$alkylene$C_{6-10}$aryl, and $C_{1-10}$alkylene$C_{3-10}$cycloalkyl.

3. The process of claim 1, wherein $R^3$ is selected from H, $C_{1-6}$alkyl, $C_{1-6}$acyl, $C_{6-10}$aryl, $C_{3-6}$cycloalkyl, $C_{3-6}$cycloalkenyl, $C_{1-6}$alkylene$C_{6-10}$aryl, and $C_{1-6}$alkylene$C_{3-6}$cycloalkyl.

4. The process of claim 2, wherein the compound of Formula I is a compound of Formula I(b):

wherein

≈ represents a single or double bond;

$R^1$ is selected from $C_{1-10}$alkyl, $C_{2-10}$alkenyl, $C_{3-10}$cycloalkyl, $C_{3-10}$cycloalkenyl, $C_{6-10}$aryl, $C_{1-10}$alkylene$C_{6-10}$aryl and $C_{1-10}$alkylene$C_{3-10}$cycloalkyl; and $R^2$ is selected from H, $C_{1-10}$alkyl, $C_{1-10}$acyl, $C_{6-10}$aryl, $C_{3-10}$cycloalkyl, $C_{1-10}$alkylene$C_{6-10}$aryl and $C_{1-10}$alkylene$C_{3-10}$cycloalkyl.

5. The process of claim 4, wherein the compound of Formula II(b) is protected prior to reaction with the reagent of Formula III under conditions to provide ketals of Formula IV:

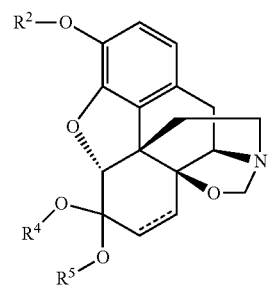
IV wherein

≈ represents a single or double bond;

$R^2$ is selected from H, $C_{1-10}$alkyl, $C_{1-10}$acyl, $C_{6-10}$aryl, $C_{3-10}$cycloalkyl, $C_{1-10}$alkylene$C_{6-10}$aryl and $C_{1-10}$alkylene$C_{3-10}$cycloalkyl; and $R^4$ and $R^5$ are each independently the same or different hydrolysable protecting group, or $R^4$ and $R^5$, together with the oxygen atom to which each is bonded, form a hydrolysable cyclic protecting group.

6. The process of claim 5, wherein the conditions to provide the ketals of Formula IV comprise adding a suitable ketone activating reagent to a stirred suspension or solution comprising the compound of Formula II(b) and a suitable alcohol, optionally in a suitable solvent, and allowing the mixture to stir for a time and temperature for the conversion of the compound of Formula II(b) to the compound of Formula IV to proceed to a sufficient extent.

7. The process of claim 5, wherein the reaction of the compound of Formula IV with the reagent of Formula III provides compounds of Formula V:

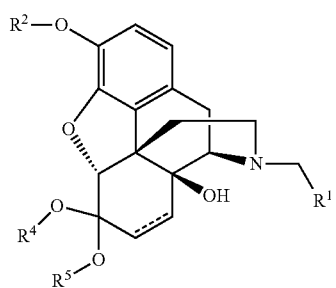

V wherein
≈ represents a single or double bond;
R$^1$ is selected from C$_{1-10}$alkyl, C$_{2-10}$alkenyl, C$_{3-10}$cycloalkyl, C$_{3-10}$cycloalkenyl, C$_{6-10}$aryl, C$_{1-10}$alkyleneC$_{6-10}$aryl and C$_{1-10}$alkyleneC$_{3-10}$cycloalkyl;
R$^2$ is selected from H, C$_{1-10}$alkyl, C$_{1-10}$acyl, C$_{6-10}$aryl, C$_{3-10}$cycloalkyl, C$_{1-10}$alkyleneC$_{6-10}$aryl and C$_{1-10}$alkyleneC$_{3-10}$cycloalkyl; and
R$^4$ and R$^5$ are each independently the same or different hydrolysable protecting group, or R$^4$ and R$^5$, together with the oxygen atom to which each is bonded, form a hydrolysable cyclic protecting group.

8. The process of claim 7, wherein deprotection of the compounds of Formula V under hydrolysis conditions provides ketones of Formula I(b):

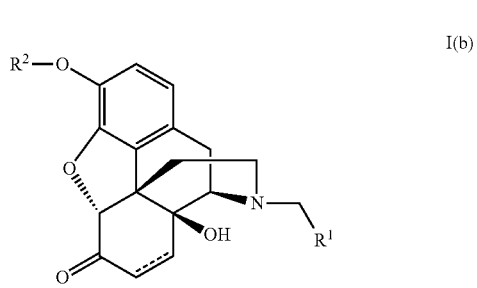

I(b)

wherein
≈ represents a single or double bond;
R$^1$ is selected from C$_{1-10}$alkyl, C$_{2-10}$alkenyl, C$_{3-10}$cycloalkyl, C$_{3-10}$cycloalkenyl, C$_{6-10}$aryl, C$_{1-10}$alkyleneC$_{6-10}$aryl and C$_{1-10}$alkyleneC$_{3-10}$cycloalkyl;
R$^2$ is selected from H, C$_{1-10}$alkyl, C$_{1-10}$acyl, C$_{6-10}$aryl, C$_{3-10}$cycloalkyl, C$_{1-10}$alkyleneC$_{6-10}$aryl and C$_{1-10}$alkyleneC$_{3-10}$cycloalkyl.

9. The process of claim 8, wherein the hydrolysis conditions to provide the compounds of Formula I(b) comprise treating the compounds of Formula V under suitable acidic conditions for a time and temperature for the conversion of the compounds of Formula V to the compounds of Formula I(b) to proceed to a sufficient extent.

10. The process of claim 9, wherein the suitable acidic conditions comprise adding about 2 N to about 6 N HCl to a stirred solution of the compound of Formula V in a suitable organic solvent.

11. The process of claim 5, wherein R$^4$ and R$^5$ are Me.

12. The process of claim 5, wherein R$^4$ and R$^5$, together with the oxygen atom to which each is bonded, and the carbon atom to which each oxygen atom is bonded, form a dioxolane moiety.

13. The process of claim 4, wherein prior to reaction with the reagent of Formula III, the compound of Formula II(b) is treated under reducing conditions to provide a compound of Formula II(a):

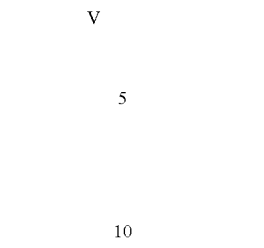

II(a)

wherein
≈ represents a single or double bond; and
R$^2$ is selected from H, C$_{1-10}$alkyl, C$_{1-10}$acyl, C$_{6-10}$aryl, C$_{3-10}$cycloalkyl, C$_{1-10}$alkyleneC$_{6-10}$aryl and C$_{1-10}$alkyleneC$_{3-10}$cycloalkyl; and
R$^3$ is H.

14. The process of claim 13, wherein the reducing conditions to provide the compound of Formula II(a) wherein R$^3$ is H comprise treating the compound of Formula II(b) in a suitable solvent with a suitable reducing agent for a time and temperature for the conversion of the compound of Formula II(b) to the compound of Formula II(a) wherein R$^3$ is H to proceed to a sufficient extent.

15. The process of claim 13, wherein the reaction of the compound of Formula II(a), wherein R$^3$ is H with the reagent of Formula III provides a compound of Formula I(a):

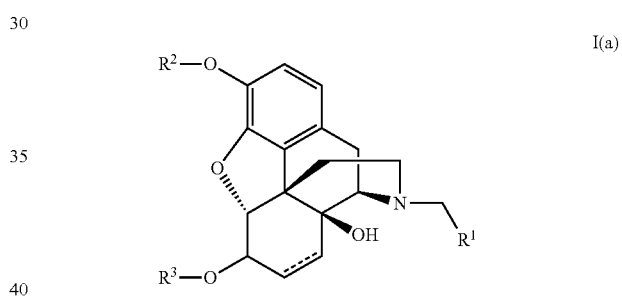

I(a)

wherein
≈ represents a single or double bond;
R$^1$ is selected from C$_{1-10}$alkyl, C$_{2-10}$alkenyl, C$_{3-10}$cycloalkyl, C$_{3-10}$cycloalkenyl, C$_{6-10}$aryl, C$_{1-10}$alkyleneC$_{6-10}$aryl and C$_{1-10}$alkyleneC$_{3-10}$cycloalkyl;
R$^2$ is selected from H, C$_{1-10}$alkyl, C$_{1-10}$acyl, C$_{6-10}$aryl, C$_{3-10}$cycloalkyl, C$_{1-10}$alkyleneC$_{6-10}$aryl and C$_{1-10}$alkyleneC$_{3-10}$cycloalkyl; and
R$^3$ is H.

16. The process of claim 1, wherein R$^1$ is selected from C$_{1-6}$alkyl, C$_{2-6}$alkenyl, C$_{3-6}$cycloalkyl, C$_{3-6}$cycloalkenyl, C$_{6-10}$aryl, C$_{1-6}$alkyleneC$_{6-10}$aryl, and C$_{1-6}$alkyleneC$_{3-6}$cycloalkyl.

17. The process of claim 1, wherein R$^2$ is selected from H, C$_{1-6}$alkyl, C$_{1-6}$acyl, C$_{6-10}$aryl, C$_{3-6}$cycloalkyl, C$_{3-6}$cycloalkenyl, C$_{1-6}$alkyleneC$_{6-10}$aryl, and C$_{1-6}$alkyleneC$_{3-6}$cycloalkyl.

18. The process of claim 1, wherein the reagent of Formula III is selected from a Grignard reagent, an organolithium reagent, an organocuprate reagent, an organozinc reagent and an organoaluminum reagent.

19. The process of claim 18, wherein the reagent of Formula III is a Grignard reagent, wherein A is MgX and X is selected from Cl, Br and I.

20. The process of claim 1, wherein the compound of Formula I is selected from a compound of Formula I(b)(i), I(b)(ii) and I(b)(iii):

I(b)(i)

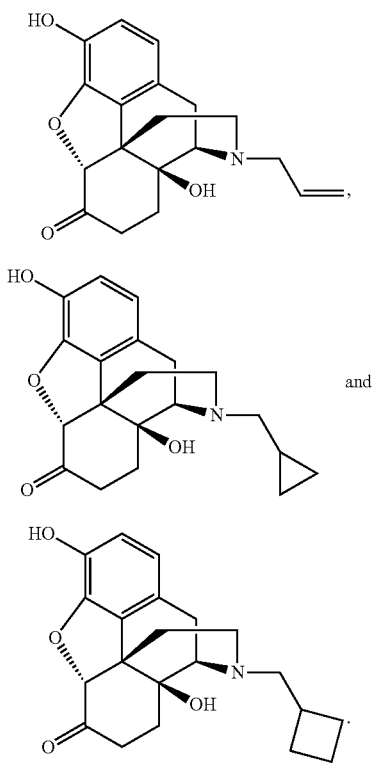

and

21. The process of claim 1, wherein the compound of Formula I is a compound of Formula I(a)(iii):

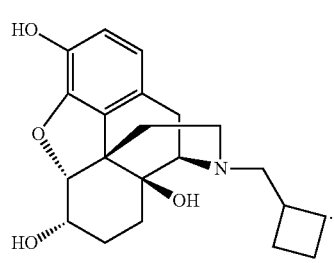

22. The process of claim 1, wherein the conditions to provide the compounds of Formula I from the compounds of Formula II using the reagents of Formula III comprise adding the reagent of Formula III dropwise to a stirred solution of the oxazolidine of Formula II in a suitable solvent at about −5° C. to about 5° C., allowing the mixture to warm up to a temperature of about 0° C. to about 30° C., and stirring for a time for the conversion of the compound of Formula II to the compound of Formula I to proceed to a sufficient extent.

23. The process of claim 22, wherein the reagent of Formula III and the compound of Formula II are used in a molar ratio of about 3:1 to about 8:1.

24. The process of claim 1, wherein the compound of Formula I is prepared from the compound of Formula II in a one-pot synthesis without the isolation of intermediates.

* * * * *